(54) FLOW ESTIMATION USING AN ULTRASONICALLY MODULATED CONTRAST AGENT

(75) Inventors: John C. Lazenby, Fall City; Jeffrey Slusher, Sultan, both of WA (US)

(73) Assignee: Siemens Medical Systems, Inc., Iselin, NJ (US)

( * ) Notice: Subject to any disclaimer, the term of this patent is extended or adjusted under 35 U.S.C. 154(b) by 0 days.

(21) Appl. No.: 09/410,169

(22) Filed: Sep. 30, 1999

(51) Int. Cl.$^7$ ........................................ A61B 08/00
(52) U.S. Cl. ........................ 600/458; 600/454; 600/437
(58) Field of Search .................................. 600/437, 440, 600/441, 443, 447, 454, 458

(56) References Cited

U.S. PATENT DOCUMENTS

| | | | |
|---|---|---|---|
| 5,385,147 | * | 1/1995 | Anderson et al. ................. 600/443 |
| 6,015,384 | * | 1/2000 | Ramamurthy et al. ............ 600/440 |
| 6,083,168 | * | 7/2000 | Hossack et al. ................... 600/443 |

* cited by examiner

Primary Examiner—Marvin M. Lateef
Assistant Examiner—Maulin Patel

(57) ABSTRACT

Reflectors such as microbubbles in a contrast agent introduced into a blood vessel of a patient are destroyed (or otherwise acoustically altered) using focused ultrasound at a modulation point according to an input modulation sequence. This creates "gaps" in the flowing contrast agent that are sensed at a downstream sensing point. The pattern of gaps is then matched in time with the input modulation sequence to determine a transit time for the gaps, which is also the flow velocity of the blood. The input modulation sequence creates at least two gaps, but may otherwise have any of several different forms, which include, among others, square-wave, maximal sequence, random binary patterns. Edge-detection and correlation techniques are used to match the input and sensed gap patterns. By triggering the input sequence off of a heart rate monitor, a flow velocity profile may also be calculated and displayed from one heart beat to the next. By also imaging the blood vessel and determining its cross-sectional area at at least one point, the invention is also able to provide a volumetric blood flow estimate.

12 Claims, 4 Drawing Sheets

FLOW ESTIMATION USING AN ULTRASONICALLY MODULATED CONTRAST AGENT

BACKGROUND OF THE INVENTION

1. Field of the Invention

This invention relates to a system and a method for determining the flow of blood in blood vessels using ultrasound and a contrast agent that is introduced into the blood stream.

2. Background Art

There is a well-known need to determine blood flow in a patient. Lower than expected flow may, for example, indicate the presence of a thrombosis or of arteriosclerosis, and sudden changes in flow, corresponding to changes in cardiac output, are important indicators in patient monitoring.

There are, accordingly, many systems for measuring blood flow. Many common systems are catheter-based, and involve injecting an indicator upstream where the flow is to be measured and then measuring the indicator concentration at a downstream position. The time of flight then determines the average flow velocity. One typical indicator is some bolus of cold fluid or marker dye. Another common indicator is heat; in such systems, a heating element is used as the upstream indicator injector and a thermistor is used as the downstream sensor.

The obvious disadvantage of these methods is their level of invasiveness—by definition, catheter-based systems involve placing a catheter into the blood vessel. For monitoring cardiac output, for example, the catheter is commonly inserted into the femoral artery, that is, below the hip, and is threaded all the way up into the right pulmonary artery adjacent to the heart. Another disadvantage is that it is not always practical or even possible to reach certain flow measurement points.

Still another shortcoming of bolus-based systems is that it is usually not possible to carry out several measurements, at least not close to each other in time. One cannot, for example, inject a long series of cold (often near zero degrees Celsius) boluses into the patient's heart without causing more severe problems than the patient may have had in the first place.

Another known method for measuring flow velocity uses ultrasound. In systems that implement this method, ultrasound generated by a transducer is focused on a region of the flow, the received echo signal is sensed by the transducer, and flow velocity is calculated as a function of the sensed Doppler shift of the received signal relative to the transmitted signal. Current practical techniques or ultrasound flow velocity estimation using such Doppler methods are, however, not sufficiently quantitative. Moreover, Doppler techniques measure the component of velocity in only a single direction.

Yet another method that has been proposed uses ultrasound together with a contrast agent that is injected into the blood stream in the region of interest. According to this approach, a high-intensity ultrasound field is used to destroy the microbubbles in the contrast agent at some upstream point in the flow. The resulting gap or "negative bolus" in the contrast agent is then tracked downstream. Measurements of the transit time from the point where the microbubbles in contrast agent are destroyed to the final measurement point then provide quantitative estimates of flow speed.

A related approach involves interrupting the high-intensity ultrasound field, which is used to destroy the contrast agent over a period of time. This then creates a "positive bolus" of contrast agent, whose progress is tracked as it passes downstream.

The main problem with these techniques is that they give only a single measurement of the time of flight of the contrast agent bolus. This makes it impossible to track changes in the flow velocity. Of course, one could simply repeat the single-bolus measurement later, using several independent boluses, but it is then uncertain whether any given measurement was taken during a period of unusually high noise, such as often arises when the patient is being artificially ventilated.

Yet another problem with single-bolus techniques is that the accuracy of the measurement depends on how well the system can identify the edges of the bolus. Even if the ultrasound beam could create an initial bolus with perfectly straight edges, that is a step-function input signal, then the edges will invariably be rounded and spread out as the bolus progresses downstream. It then becomes difficult to determine just which point of the sensed bolus is to be matched with which point of the input signal. The closer together the input and output are, the more sensitive the speed calculation will be to such errors. On the other hand, the farther apart the input and output are, the more the bolus will be deformed before being sensed at the output, What is needed is therefore a minimally invasive method that would make possible continuous or at least nearly continuous measurement of flow in order to track changes over time. The method should reduce the influence of temporary or non-representative disturbances such as ventilation noise, and it should be less sensitive to channel disturbances such as mixing and spreading than single-bolus or independent-bolus systems. This invention provides such an improved method, and a system to implement it.

SUMMARY OF THE INVENTION

Figure 1:
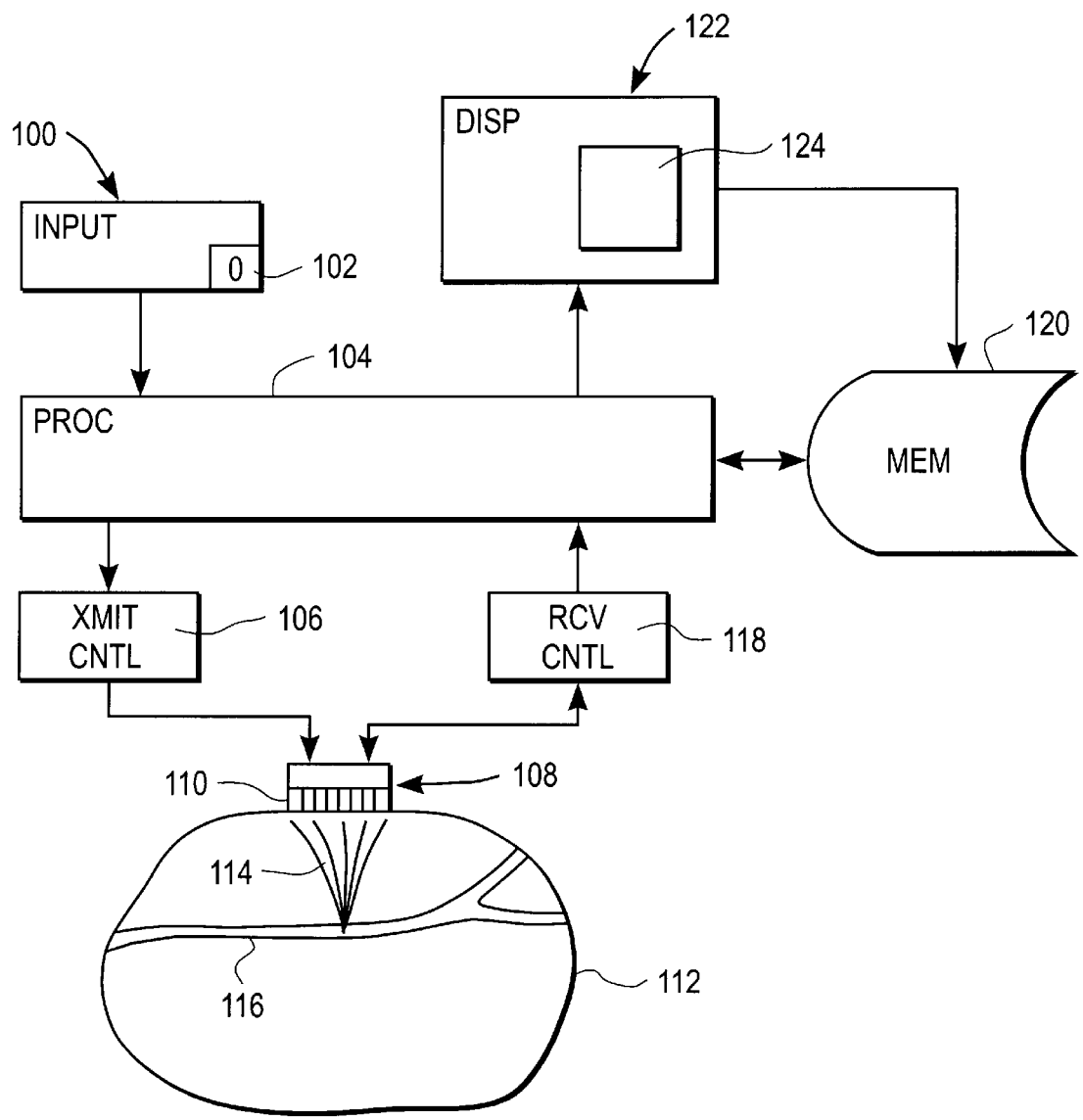
FIG. 1 shows the main components of an ultrasonic system according to the invention for determining flow velocity.

The invention determines blood flow velocity in a patient's blood vessel, into which a contrast agent has been introduced. A beam of ultrasound is focused from a transducer onto a modulation point in the blood vessel, which lies downstream from where the contrast agent has been introduced. The transducer has a high state, in which the ultrasonic beam destroys or at least significantly reduces insonified microbubbles (or changes the acoustic properties, in particular, the ultrasound reflectivity of some other reflector included in the contrast agent), and a low state, in which microbubbles (or other reflectors) pass the modulation point substantially intact. Under the control of a processing system and a transmission controller, the transducer is energized alternately between the high and low states according to a predetermined modulation sequence to create a pattern of a plurality of contrast agent gaps in which the concentration of microbubbles is reduced. The ultrasonic echo signal that is downstream in the blood vessel from the modulation point is then sensed, preferably by refocusing the transducer for transmission into and reception from the sensing point. The processing system then determines a transit time for the contrast agent, which is also the blood flow velocity, between the modulation and sensing points, by calculating a time shift function of at least a portion of the modulation sequence and a corresponding portion of the echo signal.

The steps of creating the pattern of contrast agent gaps, of sensing the ultrasonic echo signal, and of determining the transit time and blood flow velocity are preferably repeated, so that blood flow velocity can be calculated and displayed substantially continuously. The modulation sequence may have any of many different patterns, such as a square-wave signal, a maximal sequence, and even a random binary sequence.

One way of determining blood flow velocity is that the processing system first determines a time of passage of at least one gap edge in the echo signal. Here, a gap edge is defined as a transition in the contrast agent between a region having a relatively high microbubble concentration and a region having a relatively low microbubble concentration. The processing system then calculates the transit time of the contrast agent by calculating the time difference between the time of passage of the gap edge and a corresponding state transition in the modulation sequence.

Another way of calculating the blood flow velocity is for the processing system to use correlation techniques to "match" the sensed echo signal and the modulation sequence in time.

In one alternative embodiment of the invention, the patient's heart beats are also sensed, for example using a conventional heart rate monitor connected to the processing system. The processing system then calculates updates of the blood flow velocity as a function of time from one heart beat to the next. This flow rate profile may then be displayed for the user on a conventional monitor.

The invention may also be used to determine volumetric blood flow. In this extended embodiment, the cross-sectional area of the blood vessel is estimated at at least one point in the blood vessel, from the modulation point to the sensing point, inclusive. This estimation is preferably also done ultrasonically using imaging techniques. The processing system then calculates an estimate of volumetric blood flow in the blood vessel as a function of the product of the estimated cross-sectional area and the blood flow velocity.

DETAILED DESCRIPTION

This invention uses the properties of focused ultrasound to modulate a flow of a contrast agent in a unique way. This enables the system according to the invention to qualitatively measure blood flow much more accurately than is possible in existing systems. The main system components are described first. Then, the properties of ultrasound contrast agents useful to the invention are briefly described. Finally, the modulation method according to the invention is discussed, along with various alternatives.

System Components

FIG. 1 shows the main components of an ultrasonic system suitable for use in implementing the invention. The user enters various conventional scan and control parameters into an input unit 100, which typically includes such devices as a keyboard 102, knobs and buttons. The input unit is connected to a processing system 104, which will typically be an electrically connected and cooperating group of processors such as microprocessors and digital signal processors. The processing system 104 may, however, also be implemented using a single processor as long as it is fast enough to handle the various tasks described below.

As in known systems, the processing system 104 sets, adjusts, and monitors the operating parameters of a conventional transmission and control circuit 106. This control circuit 106 generates and applies electrical control and driving signals to an ultrasonic transducer 108. In the preferred embodiment of the invention, the transducer 108 includes an array 110 of individually controllable piezoelectric elements. As is well known in the art, the piezoelectric elements generate ultrasonic waves when the electrical signals are of the proper frequency are applied to them.

The transducer 108 is placed against a portion 112 of the body of a patient, and by varying the phasing, amplitude and timing of the driving signals for the transducer array elements, ultrasonic waves are focused to form a transmit beam 114. The beam is focused on an interrogation region, that is, some portion of the body that is to be imaged or, in the case of this invention, where blood (or other fluid) flow is to be measured. In FIG. 1, the body portion of interest is shown as being a blood vessel 116.

Ultrasonic echoes from the waves transmitted into the interrogation region return to the array 110 in the transducer 108. As is well understood, the piezoelectric elements in the array convert the small mechanical vibrations caused by the echoes into corresponding electrical signals. Amplification and other conventional signal conditioning is then applied to the echo signals by a reception controller 118. This processing includes, as needed, such known signal conditioning as time-gating, gain compensation, and diffraction compensation, in order to identify the echo signals from the interrogation region. The type of conventional signal processing needed will in general depend on the particular implementation of the invention and can be chosen using known design methods.

One advantage of using a multi-element transducer array 110 is that the beam of ultrasound it creates can be steered; that is, the region of maximum intensity of the ultrasonic energy transmitted by the array can be moved and focused by changing the phasing of the electrical signals applied the array elements. As will be understood from the discussion below, however, the invention can be implemented using different array structures, both linear, multi-dimensional, and annular, and even using fixed-focus single-element transducers. It is also not necessary according to the invention that the transducer 108 must be placed against the patient's body from without. Rather, the transducer may also be maneuvered inside the patient's body and the beam can be focused on the interrogation region from inside. This is the case with, for example, transesophageal probes. The only requirements are that it should be possible to change the region of focus of the transducer between two points in a region of interest, either electrically, for example, through phasing of array elements, or mechanically; to transmit ultrasonic energy sufficient to destroy microbubbles in a contrast agent at an upstream position; and to sense the relative strength of echo signals at a downstream position. It would also be possible to implement the invention using separate transducer for transmission and reception, although this has obvious practical disadvantages.

It is, moreover, not actually necessary to create an image of the interrogation region in order to determine blood flow according to the invention. On the other hand, the invention will most commonly be used in settings that require other diagnostic ultrasound procedures, including imaging. An imaging capability will also often be helpful in order to aim the transmit beam. Furthermore, it will in most cases be preferable for the user not only to get a measured value of blood flow, but also to be able to see from what body structures and positions the flow measurements are being made. The user would then be able to specifically image, for example, a portion of the body that seems to have anomalous flow velocity; conversely, the user might want the system to measure the blood flow in a region that the user identifies from an image as being of particular concern or interest. The preferred embodiment of the invention therefore is incorporated into a system that is also capable of imaging. The imaging capabilities of such a system are, moreover, used in various extended embodiments of the invention, as is described below.

The reception controller 118, all or part of which is normally integrated into the processing system 104 itself, converts the ultrasonic echo signals (which are typically at radio frequencies, on the order of a few to tens of megahertz) into lower frequency ranges for processing, and may also include analog-to-digital conversion circuitry. This is well known in the art of diagnostic ultrasound. A conventional memory 120 is also included in order to store, among other conventional data and code, a digital representation of the echo signals.

A display system 122 is preferably included in order to display for the user the flow velocity values as determined by the invention, as well as an image of the interrogation region if imaging is included along with in a given implementation of the invention. The display system preferably includes a conventional monitor 124 for displaying the flow measurements, and the image of the interrogation region, if imaging is included. Since the invention can provide a quantitative flow measurement, as opposed to the generally qualitative measurements obtained using conventional Doppler techniques, the display system 122 will typically indicate flow numerically. Flow may, however, also, or instead, be displayed graphically, for example using the color-coding often used in Doppler systems.

The display system 122 also includes known circuitry for scan conversion and for driving the display, as needed. These circuits are well known and are therefore neither specifically illustrated nor described further.

Contrast Agents

Because blood itself is such a poor reflector of ultrasound, especially relative to the tissue it flows through, it is common to inject a contrast agent into the blood stream to increase the strength of echo signals. In order to create a large number of strong acoustic impedance boundaries, ultrasonic contrast agents are liquid carriers containing a very high density, that is, concentration, of ultrasound reflectors. In most conventional contrast agents, these reflectors are very small bubbles—microbubbles—of gas. The microbubbles in the contrast agents are preferably as uniformly distributed in every volume of the contrast agent as possible.

It is not necessary according to the invention for the ultrasound reflectors to be microbubbles. Rather, any reflectors included in the contrast agent whose acoustic properties can be modified by insonification with ultrasound may be used in this invention. Since microbubbles are at present by far the most common reflectors in contrast agents, it is assumed below that such a contrast agent is used. This is, however, merely by way of example—the invention is not restricted to use with any particular type of reflector as long as the acoustic properties of the reflectors can be changed by insonification with ultrasound sufficiently to allow detection of the change using an ultrasound transducer.

When subjected to ultrasonic energy of sufficient strength and within a predetermined frequency range, the microbubbles in the contrast agent are destroyed, that is, the acoustic properties of these reflectors are changed: they collapse and lose their ability to strongly reflect ultrasound. The required intensity and frequencies are either specified by the manufacturers or can be determined using conventional experimentation.

The properties of contrast agents are well-understood in the art of diagnostic ultrasonic. In all embodiments of the invention, it is assumed that a contrast agent is injected or otherwise introduced into the stream of blood whose flow velocity the invention is to measure. The injection point may be at any point such that it will eventually reach the point (Pm) where the ultrasound is to modulate the contrast agent. This modulation is described below.

Contrast Agent Modulation

The main aspect of the method according to the invention is that the transducer 108 is used to transmit a high-intensity beam of focused ultrasound into the patient's blood stream in a region of interest, into which a contrast agent has been injected. The beam is switched on and off according to a predetermined pattern in order to create a series of regions in which the microbubbles in the contrast agent have substantially destroyed, or at least so reduced in number and concentration that the echo signal from the region is clearly distinguishable from regions in which the microbubbles have not been destroyed. In other words, a pattern of "negative" contrast agent boluses is created in the flowing blood. This pattern is sensed downstream at one or more positions, preferably using the same transducer. The transit time of the pattern, or of separate edges within the pattern, is then calculated. The velocity of the flow (of both the boluses and the blood in which the boluses are moving) is then equal to the distance between the upstream destruction and downstream sensing positions divided by the sensed transit time.

Figure 2:
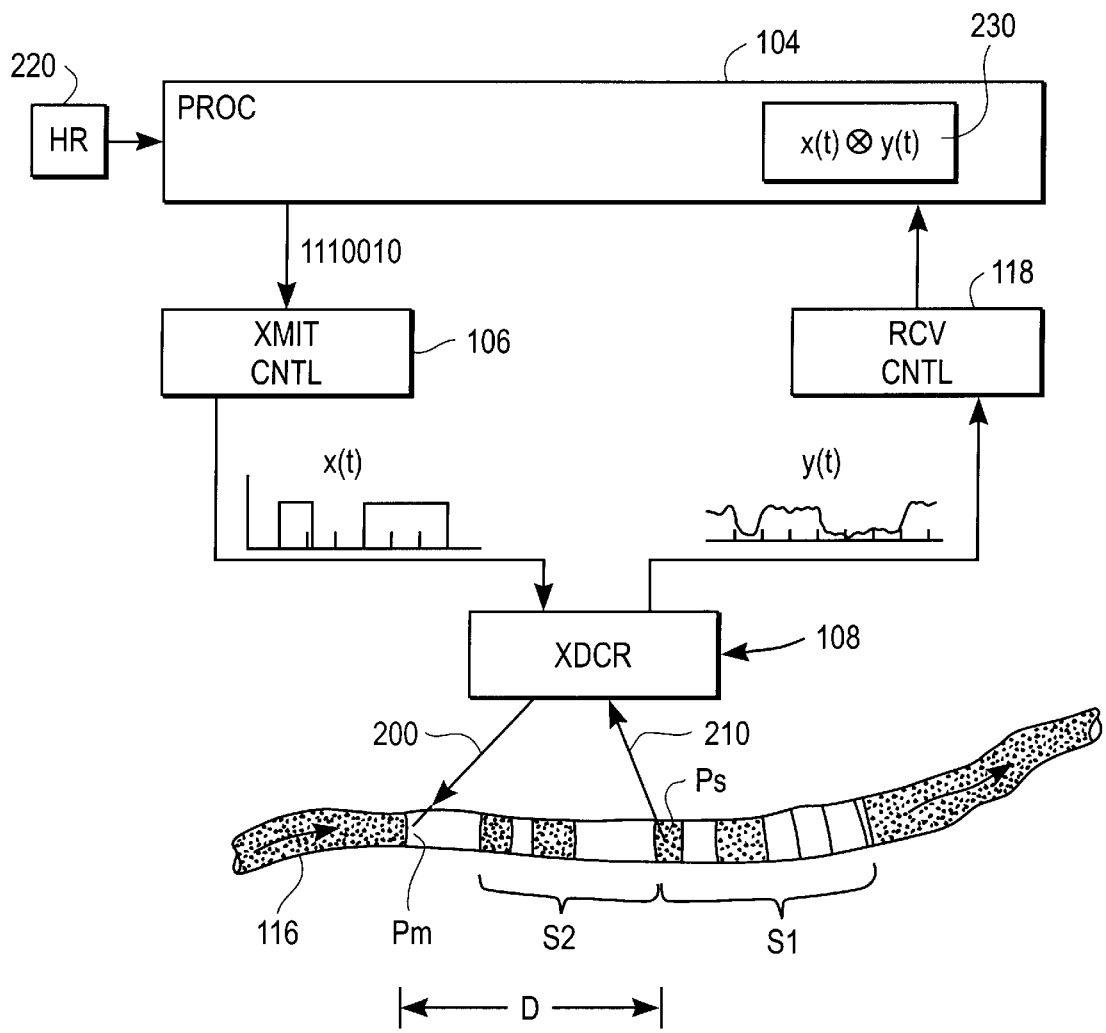
FIG. 2 illustrates the method according to the invention for determining flow using continuous contrast agent modulation.

FIG. 2 illustrates the preferred embodiment of the method according to the invention. In FIG. 2, the microbubbles of an injected contrast agent that is flowing, along with the blood, within the blood vessel 116 are indicated by dot-shading. Regions in which microbubbles have been destroyed are illustrated without the dot-shading. The direction of flow of the blood is illustrated by arrows within the blood vessel.

A beam of ultrasound is transmitted from the transducer 108 and is steered and narrowly focused, using conventional techniques, onto an upstream destruction or modulation point Pm within the blood vessel. Note that the modulation "point" will in general preferably be large enough to destroy as many microbubbles as possible over a predetermined beam width at Pm. Pm therefore does not have to be the smallest possible region of focus. The frequency and intensity of the transmit beam 200 are chosen, again using known methods (for example, in accordance with specifications provided by the manufacturer of the contrast agent), such that the microbubbles in the contrast agent are destroyed according to a predetermined sequence when subjected to the transmitted ultrasound. A sequence of "gaps" or "negative boluses" is thereby created in the flow of contrast agent. The input signal—the driving signal for the transducer—is indicated as the function x(t).

By changing the focus and steering of the transducer, the transducer then senses the echo signals 210 as an output signal y(t) from a sensing point Ps in the blood stream, which is downstream from the modulation point Pm. The switch of the transducer 108 from transmission onto the modulation point Pm to transmission into and reception from the sensing point Ps can be done using conventional steering and beamforming techniques. "Sensing" of echo signals is to be interpreted here as comprising both the transmission of ultrasound into the sensing point and reception of the echo signals from this point.

Several different methods are described below for measuring blood flow velocity at the sensing point Ps. It should be understood that the same methods may be used to sense and measure flow velocity at more than one downstream sensing point. These separate measurements could then either be displayed separately, or could be combined mathematically (for example, by averaging) to generate an average flow velocity.

In the preferred embodiment of the invention, a single transducer 108 is used both for generation of the transmit beam 200 and for sensing the echo signals 210. This is not necessary. Instead, it is possible to implement the invention using separate devices for transmission and reception.

Square-Wave Modulation

According to the simplest method of the invention, the processing system 104 directs the transmit controller 106 to activate the transducer 108 according to a simple square-wave pattern.

Note that it may not be necessary to completely de-energize the transducer in order to create an "OFF" state. In the context of this invention, the transducer is in the "OFF" or "0" state when the transmit beam 200 it generates has less than the power needed to destroy microbubbles in the contrast agent; the transducer is in the "ON" or "1" state when the transmit beam is powerful enough to destroy the microbubbles in the contrast agent in the region of focus of the transmit beam.

In other words, in the square-wave embodiment of the invention, the transmit beam 200 is energized in according to a "10101010 . . ." input sequence, which may be either continuous, or in "packets," with a finite, predetermined number of state changes. (Note that is not necessary for the ON and OFF states to be of equal duration.) This then creates a flowing pattern of roughly equidistant gaps or edges in the contrast agent. As the name implies, an "edge" is a point of transition between regions in the contrast agent with and without microbubbles, that is, from the "1" state to the "0" state, or vice versa.

The transducer focus is then switched to the downstream sensing point Ps. This can be either after the input sequence has been completed (assuming that Ps is far enough downstream from Pm to allow completion of the sequence before the first edge of the input signal (the first edge of the first contrast agent gap to reach Ps), or in an alternating manner (assuming that the transducer can be refocused fast enough to allow it to create a clear gap when transmitting in the ON state onto Pm).

The transit distance D between Pm and Ps can be determined using known methods. In short, since the angle and depth of focus of the transducer are known to (in fact, set by) the processing system 104, the points Pm and Ps are known relative to the transducer; thus, the processing system can calculate the distance from Pm to Ps using simple, known geometric and trigonometric formulas. When each edge of the square wave arrives at the downstream sensing point Ps, the processing system can calculate an estimate of its transit time—it's simply the time from when the edge was created until the time when it was sensed. Naturally, it is essential that one keep track of which edge is which—if the processing system loses track of which edge is passing the sensing point Ps, then there will be no way for the processing system to recover or "resynchronize."

The issue of synchronization, that is, of matching a transmitted input pulse in time with a sensed output pulse, is closely related to the issue of edge detection: Even if it were possible to generate a perfect, square-wave gap in the contrast agent, with perfectly sharp edges, then these edges will still be distorted by the effects of mixing, diffusion and other noise sources invariably found in flowing liquids.

Figure 3:
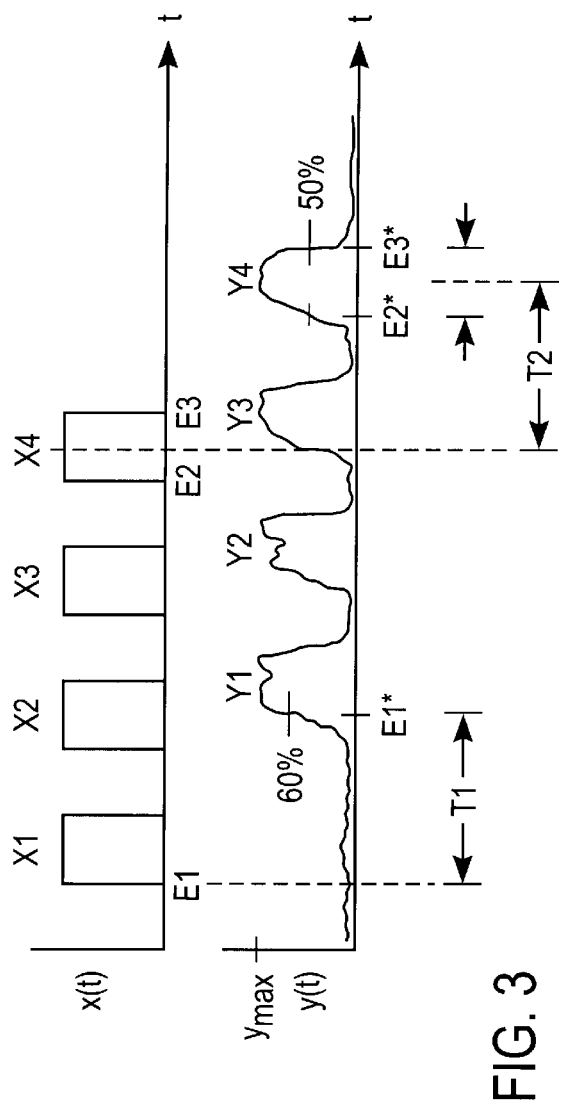
FIG. 3 illustrates the relationship between an input and output signal in a square-wave embodiment of the invention.

FIG. 3 illustrates examples of two different methods for edge detection. In this figure, a square-wave input signal x(t) is illustrated, with four square-wave input pulses X1, X2, X3, and X4, which have generated corresponding gaps in the contrast agent that are sensed as output pulses Y1, Y2, Y3, and Y4. Note that positive input energy from the transducer will lead to destruction of the microbubbles in the agent and a corresponding decrease in the sensed output amplitude.

In order better to visualize the correspondence between input and output pulses, the inverse or "negative" of the sensed output energy is graphed. Inverse values will typically also be what the processing system uses in calculations. For the sake of clarity in the description below (to avoid always having to refer to −y(t) instead of just y(t)) it is therefore assumed below that the sensed output signal is "inverted" so that the sensed output signal is in the "high" or near-maximum amplitude state when the corresponding input signal was "ON" or "1". In practice, the various methods can be implemented simply by having the processing system operate on −y(t) instead of +y(t). The inverse can be determined simply by subtracting the sensed output energy from a full-concentration baseline value, which is the sensed power from a region known to contain contrast agent with a full, normal concentration of microbubbles. A minimum-concentration baseline value can also be calculated, if needed, by operating the transducer continuously in the ON state, then sensing the power of the signal from the flow in the region known to have its microbubbles destroyed.

Alternatively, maximum and minimum return power values can be determined from the sensed output signal alone, for example by measuring (possibly with averaging) peak and minimum power values as the output signal fluctuates in response to the alternating input signal. Any such calibration method may be implemented and run either before actual flow measurements are made, or during the measurement itself. In FIG. 3, the illustrated value $y_{max}$ is the highest value assigned to the sensed output signal y(t), that is, the value of the echo signal from a region of blood with a minimum concentration of microbubbles.

Low-pass filtering of the output signal y(t) may also be included as needed in the reception controller 118 or the processing system 104 in order—by definition—to reduce the effect of any high-frequency noise. Such filtering will, however, also reduce the sharpness of the very edges that the system in many cases needs to detect. Methods are described below, however, that would work well even in "noisy" applications and even in implementations that, as a result of conventional experimentation, include low-pass filtering that smoothes edges.

In the simplest embodiment of the invention, the system determines time of transit (and thus flow velocity) by matching edges. In FIG. 3, the leading edge, occurring at time t=E1 of the first input pulse X1 corresponds to some point t=E1* on the rising slope of the sensed output pulse Y1. Note that E1 is precisely known to the system, since the processing system 104 is what is causing the pulse to be generated in the first place. The time of reception of each measured point of y(t) is also known to the system via the reception controller and the processing system, as in conventional systems. The problem is how to determine when E1* occurs. One method is for the system to determine the time at which the sensed output signal y(t) has risen to a predetermined percentage of the peak value $y_{max}$. In FIG. 3, E1* is marked where y(t) has risen to 60% of $y_{max}$. This 60% value is chosen simply by way of example; normal experimental methods may be used to determine an appropriate, reliable, accurate threshold value. Corresponding "falling" edges of x(t) and y(t) can be matched up in time in a similar fashion, for example, by marking the falling edge of y(t) at the point in time when it has fallen to the same (or some other) threshold level, for example, 60% of $y_{max}$. Once the output "edge" is determined, the time difference T1=|E1−E1*| is the transit time for the edge. The flow velocity v is then equal to D/T1 (in any chosen unit).

Of course, a single measurement of transit time may not be accurate. If a square-wave input signal x(t) is used, it is therefore preferable to determine the transit times between several input/echo edge pairs, either all "rising" edges, all "falling edges," all of both, or some combination. The system can then average these times to get an average transit time, which is divided into the distance D to calculate flow velocity v.

One advantage of measuring transit times for both rising and falling edges is that any irregularities in the different types of edges that may be caused by physical effects will tend to be averaged out. It may be, for example, that microbubbles of non-uniform size require different insonification times for destruction, so that the concentration of microbubbles in a gap may not be uniformly low. Even with completely uniform microbubbles, however, destruction may be more complete in the middle or end of an insonification period than at the beginning.

The more transitions are matched before determining flow velocity, however, the longer the measurement will take, and the more likely it will be that flow velocity will have changed during the measurement cycle. The number of transitions included can be determined using normal experimentation. Alternatively, the system could calculate and display more than one flow value, for example, an "instantaneous" flow velocity value determined by calculating the transit time of only one or a few edges, and an "averaged" flow velocity value determined by averaging the flow velocity values derived from many edges. Other schemes may also be used, such as applying a weighted (including equally weighted) moving average to the measured values.

FIG. 3 also illustrates an alternative transit-time detection method that can be used even with a square-wave (1010101010 . . . ) input signal x(t). According to this method, a threshold is set for both rising and falling edges. In the illustrated example, the input pulse X4 is sensed downstream as output pulse Y4; the threshold is chosen to be 50%. This is of course also just one possible choice— normal experimental methods may be used to determine the thresholds, which do not have to be the same. The times E2* and E3* of threshold passage of y(t) are then averaged. It is then assumed that this averaged time is the time of the maximum microbubble destruction (the "peak" of y(t)), which is matched in time with, for example, the center time of the corresponding input pulse. The transit time T2 would thus be the difference between the averaged output threshold times and the center time of the input pulse.

One way to lessen the risk of the system losing synchronization is to generate separate trains of square-wave signals. In other words, the system could generate a sequence of n pulses, then a flow velocity value is calculated as above, then a new sequence of n input pulses is generated. Any failure of synchronization will then typically not last longer than the unsynchronized sequence. Of course, every such delay also introduces leads to slower updates in the displayed flow velocity values. This may be acceptable in most applications, however.

As one alternative, a "synchronization" signal could be inserted at set periods into the blood flow. Such a synchronization signal might be, for example, an extended microbubble gap; measurements would start on the rising bubble-density "edge" at the end of the gap. Such a synchronization period will normally be included at the very beginning of flow velocity measurements in any event, at least for input sequences with short repetition rates such as a pure square-wave input sequence. Such techniques are known, for example, in the field of synchronous digital data transfer. Input sequences that are less sensitive to synchronization concerns are described below.

Modulation Frequency

The processing system 104 and transmission controller 106 together cause the transducer 108 to generate sequences of pulses of microbubble-destroying ultrasound at a particular modulation frequency f. In other words, assuming the sequence is periodic, then it will repeat with a modulation period 1/f. For a pure square-wave input signal x(t), the modulation period extends only from one rising edge of x(t) to the next. This leads to another design trade-off. The higher the modulation frequency, the more updates (transit time calculations) the system can perform in a given period. If the frequency too high, however, then the regions of destroyed contrast agent will overlap from one cycle to the next. It is therefore necessary to ensure that:

$$f < v_{min}/(2b)$$

where f is the modulation frequency, $v_{min}$ is the minimum velocity that the system is designed to resolve (which can be determined experimentally beforehand), and b is the width of the destruction beam from the transducer (or, equivalently, the width of the shortest microbubble "gap" used). For a square-wave input signal x(t), the edges of the contrast agent pulses will be detectable only if the frame rate of the downstream detection (imaging) system is at least twice the modulation frequency. With higher frame rates, it is, furthermore, possible to achieve higher precision on the transit time measurements.

Coded Input Modulation

As is mentioned above, if the system uses straightforward, square-wave input modulation, then there is no way, short of including predetermined synchronization sequences, to regain synchronization once it has been lost it: The modulation waveform is identical on each cycle, so it is impossible to tell one cycle from the next.

In "code-modulated" embodiments of the invention, a sequence of transitions is input according to a pattern with a period longer than a ON-OFF pulse pair. It then becomes possible not just to detect a transition (edge), but rather, the system is able to determine just where it is within a sequence. For example, if the system modulates with the sequence 1110010, then it would be harder to lose track of where it is (which input pulse corresponds to the immediately sensed output pulse). Making the usually accurate assumption that the blood channel can be approximated as a linear system, at least over the distance between Pm and Ps, then a transition to a "1" state after sensing, for example, a "0" output state lasting two periods can correspond only to the transition after the "00" sub-sequence in the input. Note that every transition in the sequence 1110010 is similarly unique. The timing of the duration of each sensed period can be carried out using standard clock circuitry found in the reception controller and processing system in the same way as in conventional imaging systems.

This reduction in ambiguity does not, however, come for free: With the two-symbol (two-pulse) sequence 10, there are two edges, so the average sample rate for the transit time would be once per symbol. With the seven-symbol sequence 1110010, however, there are only four edges in seven symbols, or a little more than one half sample per symbol. This means that the time needed to calculate an updated estimate of transit time (and thus blood flow velocity), on the average, is approximately twice as long as for the simple square-wave, oscillating sequence.

One particularly advantageous input sequence is a "maximal sequence." It can be shown mathematically that a maximal sequence is the longest non-repetitive sequence (having uniquely identifiable state transitions) that can be generated using a shift register with a fixed number of stages. For a shift register with n stages, for example, the maximum length sequence is $2^n-1$ symbols or "chips." The seven-symbol sequence 1110010 (described above) is a maximal sequence for a three-stage shift register. Other sequence lengths may be used in the invention; the proper length may be determined by normal experimentation. The number of edges per symbol in a maximal sequence is equal to:

$$2^{(n-1)}/(2^n-1)$$

which approaches ½ for large values of n. In other words, there is an edge for every other symbol, on average. However, within each maximal sequence there is a run of length n "1's" and a run of (n−1) "0's". By modulating the input sequence x(t) and thus generating gaps in the contrast agent according to a maximal sequence, the system according to the invention can reduce the average sample rate of the transmit time, and thus the update rate of displayed flow velocities, by a factor of two, and the worst-case wait between edges (and updates) increases will be n pulse periods.

It is easiest and has proven to be sufficiently accurate to generate the modulation sequences as gaps and pulses that are multiples of some single-pulse time. In other words, each "1" and "0" lasts as long as each other "1" and "0", respectively. This is not necessary, however. A "1" could, for example, last longer or shorter than a "0", and "1's" and "0's" themselves could be of different length. Put generally, the modulation sequence used as the input signal may be in the form:

$$H1(t1)L2(t2)H3(t3)L4(t4) \ldots Hm(tm)Ln(tn)$$

where the i'th state of the modulation sequence is either "high" (H) or "low" (L) and lasts for a time ti. Thus, the third state of the sequence is high and lasts for a time t3. If such a "time-modulated" input sequence is used, then the system will need not only to detect edges, as described above, but to time each state of the signal. These two methods will then allow the system to separate the sensed output echo signal into the correct states and match them up in time with the input sequence (which is known to the system, since it generated it). One advantage of such a time-modulated input sequence is that it will be even easier for the system to determine where in the sequence it is, since each state is essentially labeled by its duration. A disadvantage, however, is that the processing is made more complicated. A square-wave input sequence simply has t1=t2=. . . =tn.

In order to overcome the limitations of conventional single-bolus systems, the invention must, not surprisingly, operate on more than single boluses. Accordingly, the invention assumes that there are at least two contrast agent gaps either within a single multi-pulse input sequence (such as the maximal sequence), or over multiple periods of a repeating input sequence (such as the simple square-wave input sequence).

Any of the methods discussed above for edge detection may of course be used to determine transit times between input/output edge pairs, and thus flow velocity, when using maximal-length input sequences as well.

Flow Updates At Less Than Maximum Rate

In most, or at least many, situations, it will not be necessary to have a flow estimate that is updated as fast as the maximum possible rate at which the system can generate a transition (gap) in the contrast agent. Moreover, it will often be preferable to display a flow velocity rate that represents an average over some predetermined time period. Averaging of flow velocity values is mentioned above in connection with the square-wave input signal. Other forms of averaging may also be advantageous, and may be implemented using the invention.

Figure 4:
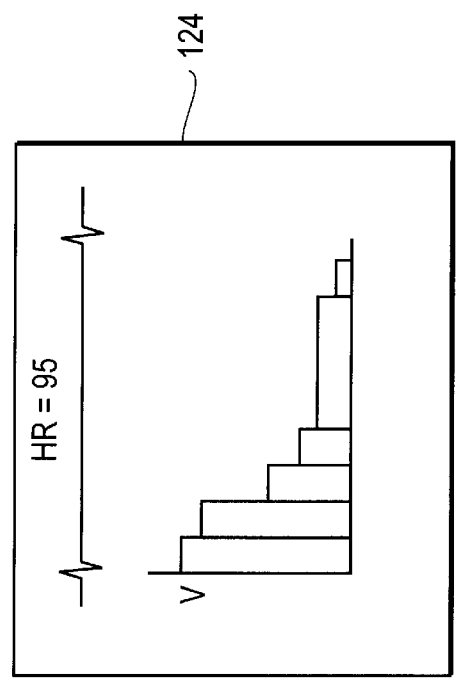
FIG. 4 illustrates an example of a display of a flow velocity profile triggered by a measured heart rate.

Depending on the contrast agent and transducer used, it may be possible to make several transit time (and thus, flow velocity) measurements during a single period of the heart beat. The system according to the invention could then be triggered to take a "suite" of measurements from one heart beat to the next. An average value could then be calculated and displayed. Alternatively, the system could display a flow velocity profile over the duration of one or more heart cycles. The system according to the invention should in such cases include or be connected to a conventional heart rate or EKG monitor 220 (FIG. 2), which generates a trigger pulse to mark for the processing system 104 the beginning and end times of measurements. This is illustrated in FIG. 4, which shows a hypothetical velocity profile between two displayed heart beats, along with a display of the current heart rate.

Correlation Methods For Encoded Modulation Sequences

The methods described above allow for the most rapid updates of the calculations of the blood flow velocity, since they generate a velocity estimate for every state transition of the input sequence. This in turn allows the system according to the invention to provide essentially continuous monitoring of the flow velocity. The accuracy of the measurements will depend, however, on the ability of the system to accurately detect edges in the sensed output signal y(t).

One way to reduce the uncertainty in detecting edges is, of course, not to have to detect them at all. By using encoded modulation sequences, the invention also makes this possible. In these embodiments of the invention, the transducer is activated, as before, to create a sequence of contrast agent gaps at the modulation point Pm. The sequence has a known length, either in number of pulses or, equivalently, in time. The sequence is timed or structured such that there is no possibility of ambiguous sequence overlapping at the sensing point Ps. In other words, either there is sufficient time between generation of consecutive modulated sequences that only one possible sequence is sensed downstream, or the sensed output sequence can be sub-divided in such a way that the sub-sequence can be uniquely matched to the input sub-sequence that caused it. The sensed output (sub-) sequence is then mathematically combined by a sub-processor or subroutine 230 (see FIG. 2) with the corresponding portion of the input signal to form a function $x(t) \otimes y(t)$ of time that is optimized. The time that yields the optimum is then taken to be the transit time.

Figure 5:
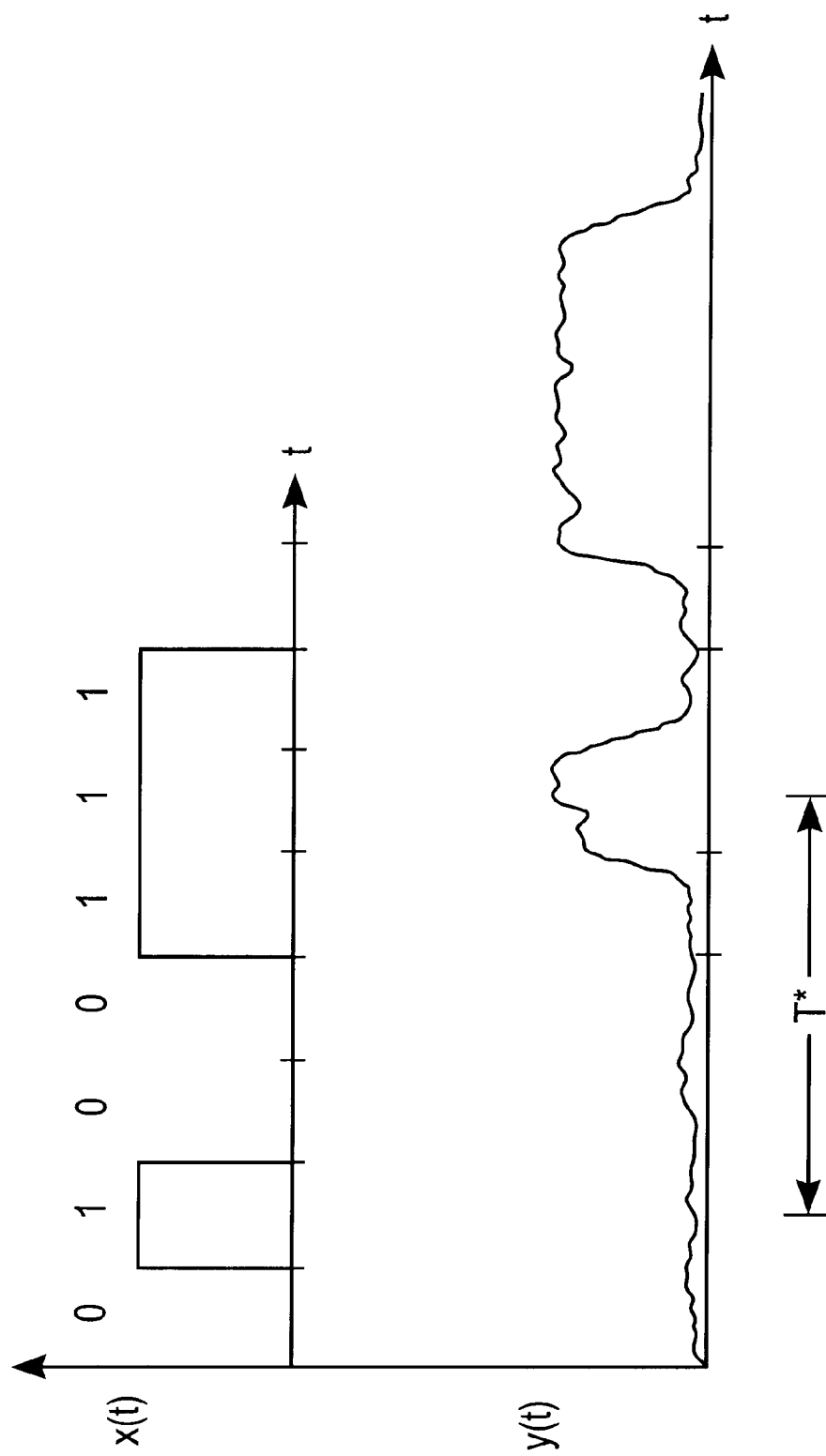
FIG. 5 illustrates a method according to the invention for determining transit times of a modulated contrast agent input signal using correlation techniques.

Assume by way of example that the contrast agent is modulated according to the maximal input sequence x(t)= 1110010. The sensed echo energy might then have a profile similar to the y(t) curve shown in the bottom half of FIG. 5. If the y(t) curve is "shifted" to the left, that is, moved "backwards" in time, then there will be a time t* (which is unrelated to the sequence period) at which it is best "matches" the input sequence x(t). This can then be assumed to be the transit time. The invention thus determines the estimate of the transit time by correlating x(t) and y(t); conventional correlation techniques may be used to determine t*, since x(t) and y(t) will both be known to the processing system.

Expressed mathematically, the system calculates the minimum of a cost function, as follows:

$$\min_{T} \int |x(t) \otimes y(t-T)|^n$$

The integral (actually, since the signals will be generated, sensed, and stored as discrete values, the "sum") is evaluated over the time period of the input sequence. The operator $\otimes$ may be simple subtraction, and for n=1 the calculation then becomes the standard minimum sum absolute difference method (MSAD). n=2 gives a least-squares metric. The exponent n may be chosen using normal experimental methods. The operator $\otimes$ may also be multiplication. Because the input signal will usually be binary, that is, "ON" ("1") or "OFF" ("0"), however, actual multiplication will not be necessary; rather, this choice is equivalent to moving a weighted-average (with weights 1 and 0) filter across the output signal and looking for the time shift that gives the greatest result.

Other operators and cost functions may of course also be used and can be determined using conventional experimental methods. The theory of cross—and auto—correlation is, for example, well known and can be applied to determine the time shift (and thus transit time) that best matches the output signal with the input signal in some predefined sense.

One advantage of matching entire sequences or sub-sequences of the input and output signals is that these methods do not depend on detecting any particular edges of the output signal. Another advantage is that the system will typically be less sensitive to noise, such as may be caused, for example, by mixing or diffusion of the contrast agent in the blood vessel, or by non-uniformities in the distribution of microbubbles in the contrast agent. Still another advantage is that the input sequence can have an almost arbitrary structure, although the more transitions, the better the "matching" procedure will generally work. For example, in addition to maximal sequences, pseudo-random or truly random binary input sequences may be used, or even just "bursts" of square-wave input sequences with a predetermined period. These advantages come at the cost of lower update rates for the calculated flow velocity values, however: instead of an update at every edge, the system will generate an update only once per complete input sequence.

In most cases, even if the input signal is a modulated sequence, then a new input signal can be generated as soon as a complete corresponding output signal is sensed. All embodiments of the invention can still generate an estimate of the flow velocity in a substantially continuous manner, in the sense that the system will display for the user updated, quantitative flow velocity values as fast as will be needed in almost all normal circumstances.

Volumetric Flow Calculations

The embodiments of the invention described above provide accurate estimates of the blood (or other fluid) flow velocity, measured from point Pm to point Ps in the vessel. As is well known, the volume of a fluid passing perpendicularly through a region is equal to the area of the region multiplied by the flow velocity. The invention can therefore be extended to provide a volumetric flow measurement in addition to the flow velocity as long as the system also includes a way to determine the cross-sectional area of the vessel at some appropriate point. If the vessel is known to have an essentially constant cross-section over the entire length of the channel (the portion of the vessel between Pm and Ps, inclusive), then any point will be as good as any other. Over the channel lengths that will normally be found in applications of the invention, this will usually be a valid assumption. Otherwise, even if the area is measured at a single point in the channel, then the volumetric measurement will be based on an average flow velocity for the channel, since transit times for the contrast agent are for flow through the entire channel from Pm to Ps. This will still provide valuable information about changes, especially if the volumetric measurements are displayed as a function of time, for example, from heart beat to heart beat, as in the embodiment described above.

Normal ultrasonic imaging methods may be used to determine a suitable section of the vessel for volumetric measurement. Measurements may also be taken at several points, and an average value can be calculated and displayed along with the measurement parameters of vessel cross-sectional area (or diameter, if it is assumed to be round), and flow velocity.

One way to determine the cross-sectional area of the blood vessel would be to use conventional imaging techniques to measure the internal diameter d of the vessel. The area A could then be approximated as $A = \pi \cdot (d/2)^2$ and a value V of volumetric flow could be calculated as $V = v \cdot A$, where v is the flow velocity calculated using any of the methods described below. Another method would be to image the entire cross section of the vessel at the chosen measurement point and then to calculate the cross-sectional area directly—this would not rely on the assumption that the vessel is perfectly cylindrical. One known system and method that could be used to determine the inner diameter of the blood vessel, with no need to assume a circular cross section, is described in U.S. Pat. No. 5,588,435 (Weng, et al., "System and Method for Automatic Measurement of Body Structures," Dec. 31, 1996).

"Inverse" Signals

In all of the embodiments of the invention described above, ultrasound is used to create "gaps" in a substantially uniform stream of microbubbles. In other words, the system according to the invention creates "0's" in an otherwise constant stream of "1's". It is of course also possible for the system to generate the input signals as the "1's" complement of the sequences described above. As long as the sensed output signal is properly converted to represent a "1" when the corresponding input pulse was also a "1", then the described methods will work just as well, although the duty cycle of the transducer (the percentage of time when it is energized or "ON") may be slightly higher for certain input sequences. For example, the 1110010 input sequence would simply become 0001101, with one more "gap" (four) per seven-pulse period than before. Such signal inversion may be done deliberately using microbubble reflectors. It may also arise if the ultrasonic reflectivity of a reflector used in a given contrast agent actually increases when subjected to sufficiently strong or properly tuned ultrasound. The modifications to the various signal detection and transit time calculations needed to handle such signal "inversion" will be obvious to anyone skilled in the art of signal processing.

What is claimed is:

1. A method for determining blood flow velocity in a blood vessel of a patient, comprising the following steps:

introducing a contrast agent into the blood vessel upstream from a modulation point, the contrast agent comprising a liquid carrier containing a concentration of ultrasound reflectors;

focusing a beam of ultrasound from a transducer onto the modulation point, the transducer having a high state, in which the ultrasonic beam significantly changes the ultrasound reflectivity of the insonified reflectors, and a low state, in which the reflectors pass the modulation point substantially unchanged;

energizing the transducer alternately between the high and low states according to a predetermined modulation sequence, thereby creating a pattern of a plurality of contrast agent gaps in which the reflectivity of the reflectors is changed;

from a sensing point in the blood vessel that is downstream from the modulation point, sensing an ultrasonic echo signal; and determining a transit time of the contrast agent, and thus the blood flow velocity, between the modulation and sensing points, by calculating a time shift function of at least a portion of the modulation sequence and a corresponding portion of the echo signal.

2. A method as in claim 1, in which the steps of creating the pattern of contrast agent gaps, of sensing the ultrasonic echo signal, and of determining the transit time and blood flow velocity are repeated substantially continuously.

3. A method as in claim 1, in which the modulation sequence is a square-wave signal.

4. A method as in claim 1, in which the modulation sequence is a maximal sequence.

5. A method as in claim 1, in which the modulation sequence is a random binary sequence.

6. A method as in claim 1, in which the step of determining the transit time comprises the following sub-steps:

determining a time of passage of the at least one gap edge in the echo signal, a gap edge being a transition in the contract agent between a region having a relatively high reflector concentration and a region having a relatively low reflector concentration; and determining the transit time of the contrast agent by calculating the time difference between the time of passage of the gap edge and a corresponding state transition in the modulation sequence.

7. A method as in claim 1, in which the step of determining the transit time of the contrast agent comprises correlating the sensed echo signal and the modulation sequence.

8. A method as in claim 1, further including the following steps:

sensing the heart beats of the patient; and calculating and displaying updates of the blood flow velocity as a function of time from one heart beat to the next.

9. A method as in claim 1, further including the following steps:

estimating a cross-sectional area of the blood vessel at at least one point in the blood vessel located from the modulation point to the sensing point, inclusive; and calculating an estimate of volumetric blood flow in the blood vessel as a function of the product of the estimated cross-sectional area and the blood flow velocity.

10. A system for determining blood flow velocity in a blood vessel of a patient, into which blood vessel a contrast agent has been introduced, the contrast agent comprising a liquid carrier containing a concentration of ultrasound reflectors; comprising:

a transducer focusing a beam of ultrasound into the blood vessel at a modulation point that lies downstream from where the contrast agent has been introduced, the transducer having a high state, in which the ultrasonic beam significantly changes the ultrasound reflectivity of the insonified reflectors, and a low state, in which the reflectors pass the modulation point substantially unchanged;

transmission control means for energizing the transducer alternately between the high and low states according to a predetermined modulation sequence, thereby creating a pattern of a plurality of contrast agent gaps in which the concentration of reflectors is reduced;

echo sensing means for sensing an ultrasonic echo signal from a sensing point in the blood vessel that is downstream from the modulation point; and processing means for determining a transit time of the contrast agent, and thus the blood flow velocity, between the modulation and sensing points, by calculating a time shift function of at least a portion of the modulation sequence and a corresponding portion of the echo signal.

11. A system as in claim 10, further including:

a heart beat monitor; and a display;

the processing means being further provided for calculating and displaying updates of the blood flow velocity as a function of time from one monitored heart beat to the next.

12. A system as in claim 10, further including area estimation means for estimating a cross-sectional area of the blood vessel at at least one point in the blood vessel located from the modulation point to the sensing point, inclusive;

the processing means being further provided for calculating an estimate of volumetric blood flow in the blood vessel as a function of the product between the estimated cross-sectional area and the blood flow velocity.

* * * * *